United States Patent [19]
Okamura et al.

[11] Patent Number: 5,869,319
[45] Date of Patent: Feb. 9, 1999

[54] BILE ACID-CONVERTING MICROORGANISM BACILLUS SP. AND A METHOD OF USE

[75] Inventors: Akio Okamura; To-oru Ogata; Hiromi Kimura, all of Tokyo, Japan

[73] Assignee: Tokyo Tanabe Company Limited, Tokyo, Japan

[21] Appl. No.: 875,778

[22] PCT Filed: Jan. 31, 1996

[86] PCT No.: PCT/JP96/00182

§ 371 Date: Aug. 5, 1997

§ 102(e) Date: Aug. 5, 1997

[87] PCT Pub. No.: WO96/24659

PCT Pub. Date: Aug. 15, 1996

[30] Foreign Application Priority Data

Feb. 6, 1997 [JP] Japan .................................. 7-017636

[51] Int. Cl.$^6$ ............................... C12N 1/20; C12P 7/42
[52] U.S. Cl. ...................... 435/252.31; 435/146
[58] Field of Search ............................. 435/146, 252.31

[56] References Cited

U.S. PATENT DOCUMENTS 4,303,754  12/1981  Macdonald ................................. 435/52

FOREIGN PATENT DOCUMENTS 404278096  10/1992  Japan .

OTHER PUBLICATIONS

Bergey's Manual of Determinative Bacteriology. Ninth Edition. 1994. pp. 559–562.

Bergey's Manual of Determinative Bacteriology. Eight Edition. 1974. pp. 557–559.

J.D. Sutherland, et al., "The Enzymic and Chemical Synthesis of Ursodeoxycholic and Chenodeoxy From Cholic Acid", Preparative Biochemistry, 12(4) pp. 307–321, 1982.

I.A. Macdonald, et al., "Formation of urso–and ursodeoxycholic acids from primary bile acids by Clostridium absonum", Journal of Lipid Research, vol. 22, pp. 458–466, 1981.

J.D. Sutherland, et al., "Formation of urso–and ursodeoxycholic acids from primary bile acids by a Clostridium limosum soil isolate", Journal of Lipid Research, vol. 25, pp. 1084–1089, 1984.

Noriyuki Masuda, et al., "A Mass Spectrometrical study of the Epimerization of the 7–Hydroxy Group in Primary Bile Acids by the Combined Action of 7α– and 7β– Dehydrogenating Organisms", Acta Med. Univ. Kagoshima, 24 (1), pp. 31–38, 1982.

Seiju Hirano, et al., "7β–Hydroxysteroid Dehydrogenase Activity among Intestinal Microorganisms, Particularly of Eubacterium aerofaciens", Acta Med Univ. Kagoshima., 24 (1), pp. 43–47, 1982.

Taiko Akao, et al., "Purification and Characterization of 7β–Hydroxysteroid Dehydrogenase from Ruminococcus sp. Of Human Intestine", J. Biochem. vol. 103, No. 3, pp. 613–619, 1987.

Shinichi Nakamura, et al., "Isolation of Clostridium absonsum from a Case of Gas Gangrene", Microbiol. Immunol., vol. 23 (7), pp. 685–687, 1979.

M. Hayase, et al., "Isolation of Clostridium absonum and Its Cultural and Biochemical Properties", Infection and Immunity, vol. 9, No. 1, pp. 15–19, Jan. 1974.

R.E. Buchanan, et al., "Bergey's Manual of Determinative Bacteriology", Eighth Edition, 1974, pp. 557–559.

*Primary Examiner*—Sandra E. Saucier
*Assistant Examiner*—Vera Afremova
*Attorney, Agent, or Firm*—Griffin, Butler, Whisenhunt & Szipl, LLP

[57] ABSTRACT

Bacillus sp. TTUR 302 which belongs to the genus Bacillus and is capable of converting bile acids having a 7α-hydroxyl group or a 7-keto group into bile acids having a 7β-hydroxyl group; and a process for producing bile acids having a 7β-hydroxyl group which comprises incubating this microorganism in an enriched medium containing bile acids having a 7α-hydroxyl group or a 7-keto group and collecting the formed bile acids having a 7β-hydroxyl group (ursodeoxycholic acids, etc.). The process is easy to operate and safe as compared with the conventional chemical synthesis method. It is also superior to the conventional microbial methods particularly in the case of industrial production, since the microorganism of the invention is a facultative anaerobe and thus capable of effecting the conversion of the bile acids under aerobic conditions at a high substrate concentration. Moreover, the microorganism shows neither any hemolytic properties nor lecithinase productivity which might result in pathogenicity.

9 Claims, No Drawings

BILE ACID-CONVERTING MICROORGANISM BACILLUS SP. AND A METHOD OF USE

This application is a 371 of PCT/JP96/00182 filed Jan. 31, 1996.

FIELD OF THE INVENTION

The present invention relates to a microorganism which is capable of converting bile acids having a 7α-hydroxyl group or a 7-keto group into bile acids having a 7β-hydroxyl group such as 3α, 7β-dihydroxy-5β-cholanic acid (referred to hereinafter as "ursodeoxycholic acid") which is useful as a cholagogue and a method for producing bile acids having a 7β-hydroxyl group utilizing said microorganism.

BACKGROUND ART

As a chemical production method for converting a 7α-hydroxyl group of bile acids into a 7β-hydroxyl group, there is known a method in which a 7α-hydroxyl group is oxidized into a 7-keto group which is then reduced to a 7β-hydroxyl group.

As a microorganism which is capable of converting a 7α-hydroxyl group of bile acids into a 7β-hydroxyl group, there are known *Clostridium absonum* (U.S. Pat. No. 4,303,754 and Journal of Lipid Research, 22, 458–465 (1981)) and *Clostridium limosum* (Journal of Lipid Research, 25, 1084–1089 (1984)). In addition, as a microorganism which is capable of converting a 7-keto group of bile acids into a 7β-hydroxyl group, there are known Peptostoreptococcus productus isolated as an enterobacterium (Acta Med. Univ. Kagoshima., 24 (1), 31–8 (1982)), *Eubacterium aerofaciens* (Acta Med. Univ. Kagoshima., 24 (1), 43–7 (1982)), and Ruminococcus sp. PO1-3 (J. Biochem. Toyama Medical and Pharmaceutical University, 102, 613–619 (1987)).

However, when a chemical production method is used to oxidize a 7α-hydroxyl group into a 7-keto group, some of the hydroxyl groups (for example, 3α-hydroxyl group) other than the 7α-hydroxyl group are simultaneously oxidized. Those hydroxyl groups, therefore, need to be protected in such cases. Furthermore, in the reduction reaction of a 7-keto group into a 7β-hydroxyl group, the use of metal sodium is common and therefore the method has a risk of explosion. The method, therefore, has some efforts to resolve in terms of handling and safety.

In the method for producing bile acids having a 7β-hydroxyl group by means of a microorganism, the organisms used such as *Clostridium absonum, Clostridium limosum, Peptostoreptococcus productu, Eubacterium aerofaciens*, and Ruminococcus sp. can grow only at low concentrations of bile acids and besides the conversion efficiency of the bile acid is low, too. Therefore, it was impossible to manufacture bile acids on a commercial scale. For example, the substrate concentrations at which *Clostridium absonum* and *Clostridium limosum* convert 3α, 7α, 12α-trihydroxy-5β-cholanic acid (referred to hereinafter as "cholic acid") into 3α, 7β, 12α-trihydroxy-5β-cholanic acid (referred to hereinafter as "ursocholic acid") at a conversion efficiency of 60% or greater are 0.06% (w/v) and 0.4% (w/v), respectively, and those at which the above organisms convert 3α, 7α-dihydroxy-5β-cholanic acid (referred to hereinafter as "chenodeoxycholic acid") into ursodeoxycholic acid at a conversion efficiency of 60% or greater are 0.02% (w/v) and 0.04% (w/v), respectively (Journal of Lipid Research, 22, 458–465 (1981); Journal of Lipid Research, 25, 1084–1089 (1984)). In addition, these organisms are strict anaerobes and hence cannot grow in the presence of oxygen. Substitution with nitrogen, therefore, is required at the time of culturing them in order to avoid contact with the air or to expel oxygen, thus necessitating special handling and equipment.

Furthermore, since *Clostridium absonum* has a pathogenically of causing gas gangrene symptoms, though weak, in the infected humans (Microbiol. Immunol., 23 (7), 685–687 (1979)), care must be taken in its handling in the commercial production. The pathogenic nature is largely due to the hemolysis-causing and lecithinase-producing ability (Journal of Lipid Research, 22, 458–465 (1981), and Infection and Immunity, 9, 15–19 (1974)). Thus, Clostridium limosum which also has the above-mentioned ability (BERGEY'S MANUAL OF DETERMINATIVE BACTERIOLOGY Eighth Edition, 557–559 (1974)) has a potential risk of showing the same pathogenicity.

DISCLOSURE OF THE INVENTION

Considering the above facts, the inventors have carried out an intensive study on the microorganisms having ability of converting a hydroxyl group of bile acids, and have discovered a novel microorganism belonging to the genus Bacillus which is capable of converting, at a high conversion efficiency, bile acids having a 7α-hydroxyl group or a 7-keto group into bile acids having a 7β-hydroxyl group even at the aerobic conditions in the growth medium containing such a high concentration of bile acid salts where ordinary microorganisms cannot grow, and have accomplished the present invention.

Thus, in accordance with the present invention, there are provided a microorganism which is capable of converting bile acids having a 7α-hydroxyl group or a 7-keto group into bile acids having a 7β-hydroxyl group, and a method for producing bile acids having a 7β-hydroxyl group, said method comprising culturing said microorganism in a nutrient medium containing bile acids having a 7α-hydroxyl group or a 7-keto group to produce bile acids having a 7β-hydroxyl group in the culture, and harvesting it.

The inventors have isolated from a soil at Ashikaga City in Tochigi prefecture of Japan a new facultative anaerobic microorganism, belonging to the genus Bacillus, that vigorously grows in a growth medium containing a high concentration of bile acid salts in which ordinary microorganisms cannot grow and that shows a facultative anaerobic nature of being able to grow both in the presence and in the absence of oxygen, said microorganism having the ability of converting bile acids having a 7α-hydroxyl group or a 7-keto group into bile acids having a 7β-hydroxyl group. The inventors have designated the microorganism as Bacillus sp. TTUR 302 and said organism was deposited on Nov. 11, 1994 with the Ministry of International Trade and Industry Fermentation Research Institute Agency of Industrial Science and Technology, of 1-3, Higashi 1-chome, Tsukuba city, Ibalaki pref., Japan (zip code 305) (FERM BP-4882).

This Bacillus sp. TTUR 302 (referred to hereinafter as "the invention organism") which is capable of converting bile acids having a 7α-hydroxyl group such as cholic acid and chenodeoxycholic acid etc. and bile acids having a 7-position keto group such as 3α-hydroxy-7-keto-5β-cholanic acid (referred to hereinafter as "7-ketolithocholic acid"), 3α, 12α-dihidroxy-7-keto-5β-cholanic acid (referred to hereinafter as "7-ketodeoxycholic acid"), 3α-hydroxy-7, 12-diketo-5β-cholanic acid (referred to hereinafter as "7, 12-diketolithocholic acid") and 3, 7, 12-triketo- 5β-cholanic acid (referred to hereinafter as "dehydrocholic acid") by using the same as the substrate into bile acids having a 7β hydroxyl group, but it does not have the ability of catabolizing or decomposing the substrate bile acid.

The substrate concentration at which the invention organism converts cholic acid into ursocholic acid at a conversion efficiency of 60% or higher is 5% (w/v), and that at which the invention organism converts chenodeoxycholic acid into ursodeoxycholic acid at a conversion efficiency of 60% or higher is 0.2% (w/v), demonstrating the fact that the invention organism can convert bile acids at a practical conversion efficiency at a high substrate concentration.

Furthermore, since the invention organism is a facultative anaerobe, it does not require special handling or equipment that is required when dealing with an anaerobic bacterium, thus simplifying the method of handling and culturing the microorganism.

In addition, as is shown in Table 3, the invention organism does not exhibit the hemolytic action and/or the ability of forming lecithinase that are responsible for the pathogenicity of infecting humans and causing gas gangrene symptoms in the infected humans, and thus the invention organism is safe in handling and culturing.

The invention organism was isolated from the soil in the following manner:

A small amount of the soil was suspended into a culture medium (glucose 0.1%, peptone 0.5%, and potassium phosphate dibasic 0.2%) containing 3% sodium cholate and was incubated at 30° C. for six days. The culture was analyzed by the thin layer chromatograpy (TLC) described below. A portion (corresponding to about 5%) of the culture liquid that formed ursocholic acid was inoculated in the medium of the same composition containing 3% sodium cholate and was incubated at 30° C. for two days. One platinum loopful of the culture liquid that formed ursocholic acid determined by the TLC is streaked on the nutrient agar plate to obtain pure bacterial isolates. Each of the isolates was cultured in the culture medium (glucose 0.2%, polypeptone 0.5%, yeast extracts 0.5%, potassium phosphate dibasic 0.1%, magnesium sulfate heptahydrate 0.02%, and sodium carbonate 0.01%, pH 8) containing 5% sodium cholate at 37° C. for three days to obtain those isolates which have a high efficiency of conversion from cholic acid to ursocholic acid as determined by measurement of ursocholic acid in the culture.

The microbiological characteristics of the invention organism are described below. These tests and taxonomy were carried out in accordance with "BERGY'S MANUAL OF Systematic Bacteriology."

The microbiological characteristics of the TTUR 302 organism

| (a) Morphological characteristics | |
|---|---|
| 1) Shape and size | 0.4–0.6 by 1.2–3.1 μm, rod-shape |
| 2) Arrangement | None |
| 3) Motility | Motile, poritrichous |
| 4) Spore | Produces ovoid spores with a size of 0.6–0.8 by 0.9–1.1 μm at the apical and subapical position, sporangium swells |
| (b) Cultural characteristics | |
| 1) Meat extract agar plate | Spherical, raised, transparent and glistening at the entire margins |
| 2) Meat extract broth | Grows, slightly turbid with sediments |
| 3) Meat extract gelatin stab | seldom liquefied |

| -continued | |
|---|---|
| culture | |
| 4) Litmus milk | Little changes observed |
| (c) Physiological characteristics | |
| 1) Gram stain | Undetermined |
| 2) Nitrate reduction | Negative (not reduced) |
| 3) Denitrification | Negative (no denitrification reaction observed) |
| 4) MR test | Negative (no color change of methyl red to red is observed) |
| 5) VP test | Negative |
| 6) Indole production | Not produced |
| 7) Hydrogen sulfite production | Produced (medium darkens) |
| 8) Starch hydrolysis | Negative (not hydrolyzed) |
| 9) Citrate utilization | |
| Koser's medium | Not utilized |
| Christensen's medium | Not utilized |
| 10) Utilization of inorganic nitrogen sources | |
| Sodium nitrate | Not utilized |
| Ammonium sulfate | Not utilized |
| Sodium glutamate | Not utilized |
| 11) Pigment production | Not produced |
| 12) Urease | Negative |
| 13) Oxidase | Negative |
| 14) Catalase | Negative |
| 15) Growth range | |
| Growth pH | Grows at pH 5.8–9.5 with optimal pH at 7–9 |
| Growth temperature | Grows at 15–50° C. with optimal temperature at 30–37° C. |
| 16) Behavior toward oxygen | Facultative anaerobe |
| 17) O-F test | Produced slight acid, no gas |
| 18) Esculin hydrolysis | Positive (hydrolyzed) |
| 19) Hemolysis | Negative |
| 20) Lecithinase | Negative |
| 21) Lipase | Negative |
| 22) Acid and gas production from sugar | |

| Sugar | Acid production | Gas production |
|---|---|---|
| L-arabinose | + | − |
| D-xylose | + | − |
| D-glucose | +/− | − |
| D-mannose | +/− | − |
| D-fructose | +/− | − |
| D-galactose | +/− | − |
| Maltose | − | − |
| Sucrose | − | − |
| Lactose | − | − |
| Trehalose | − | − |
| D-sorbitol | − | − |
| D-mannitol | − | − |
| Inositol | − | − |
| Glycerin | − | − |
| Starch | − | − |

From the above-mentioned tests, it is believed that the invention organism belongs to the genus Bacillus since it is a spore-forming facultative anaerobe. However, it is different from the common Bacillus microorganisms since it does not produce catalase.

Furthermore, in a comparative study with B. larvae, B. lentimorbus, B. popilliae and the like, Bacillus organisms that are known to grow in an anaerobic manner, differences were noted in such characteristics as growth temperature, growth pH, nutrient requirement and the like, as shown in Table 4 below.

Comparison of major characteristics of the organisms

| Microorganism | B. sp. TTUR302 | B. larvae | B. lentimorbus | B. popilliae |
|---|---|---|---|---|
| Anaerobic growth | + | + | + | + |
| Catalase | − | − | − | − |
| Gelatin liquefaction | − | + | − | − |
| Growth in meat extract broth culture | + | − | − | − |
| Growth temperature | 15–50° C. | 25–40° C. | 20–35° C. | 20–35° C. |
| Acid production from sugar | | | | |
| D-glucose | +/− | + | + | + |
| L-arabinose | + | − | − | − |
| D-xylose | + | − | − | − |
| D-mannitol | − | +/− | − | − |

It is appropriate, therefore, to assign the invention organism to a new bacterial species.

In accordance with the present invention, bile acids having a 7β-hydroxyl group can be produced by culturing a microorganism having the ability of producing bile acids having a 7-β group such as ursodeoxycholic acid in a nutrient medium containing bile acids having a 7α-hydroxyl group or a 7-keto group.

The bile acid having a 7α-hydroxyl group includes cholic acid, 3α,7α-dihydroxy-12-keto-5β-cholanic acid and chenodeoxycholic acid; the bile acid having a 7-keto group includes 7-ketolithocholic acid, 7,12-diketolithocholic acid, and dehydrocholic acid, and; the bile acid having a 7β-hydroxyl group includes ursocholic acid, 3α, 7β-dihydroxy-12-keto-5β-cholanic acid (referred to hereinafter as "12-ketoursodeoxycholic acid"), and ursodeoxycholic acid.

The concentrations of bile acids having a 7α-hydroxyl group and bile acids having a 7-keto group in the nutrient medium are in, but not limited to, the range of 0.1 to 50% (w/v) and preferably 0.2 to 5% (w/v).

The culture medium as used herein may be any medium that permits propagation of the invention organism by culturing in said medium and includes, for example, as the carbon source various carbohydrate materials such as glucose, fructose, maltose, sucrose, glycerin, starch, bran, molasses, etc., and as the nitrogen source the organic nitrogen such as peptone, meat extracts, yeast extracts, corn steep liquor, soybean meal, rape seed oil cake, various amino acids, aminosugars etc. and the inorganic nitrogen such as ammonium nitrate, ammonium chloride, sodium nitrate, etc. Furthermore, it is preferred to add, in addition to the above, traces of inorganic metal salts, vitamins, growth factors, and the like.

The invention organism may be cultured under the aerobic or anaerobic conditions. Under the aerobic condition, it is cultured by aerated agitation or by shaking in a reciprocating manner. Under the anaerobic condition, it may be cultured using, for example, equipment such as "Gaspack" etc.

The cultivation temperature is set at 20° to 40° C., pH of the culture liquid is adjusted to 5–10 preferably between pH 8–10 with sodium hydroxide etc. and the cultivation is continued for one to six days.

As a means to harvest the desired bile acid having a 7β-hydroxyl group, the bacterial mass and unwanted components in the culture are first removed by filtration or centrifugation, and then the resultant filtrate or the supernatant is acidified with the addition of hydrochloric acid or sulfuric acid to precipitate the formed bile acid having a 7β-hydroxyl group. In another method, the precipitate is separated by filtration and subjected to recrystalization to obtain the highly purified bile acid having a 7β-hydroxyl group.

THE BEST MODE FOR CARRYING OUT THE INVENTION

The present invention will now be explained with reference to the following examples, but it is to be understood that the scope of the invention is not limited by those examples in any way.

In each example, the products were identified by the thin layer chromatography or high performance liquid chromatography under the following conditions:
(1) Thin layer chromatography
  Carrier: Kieselgel 60 (0.25 mm thick, manufactured by Merck)
  Developing solvent: Chloroform/isopropanol/acetic acid (7/2/1, volume ratio)
  Color development: Phosphomolybdic acid-sulfuric acid reagent (one gram of phosphomolybdic acid is dissolved in 20 ml of methanol, to which one ml of concentrated sulfuric acid was added) is sprayed and heated until the bile acid spots turn dark blue.
(2) High performance liquid chromatography
  Column: Inertosyl ODS column (column size 4.6 φ by 250 mm, manufactured by GL Science)
  Mobile phase: Methanol/purified water/phosphoric acid (60/40/0.02M, weight ratio), flow rate: 1.0 m/min
  Detection: differential refraction

EXAMPLE 1

Two grams of glucose, 5 g of polypeptone, 5 g of yeast extracts, 1 g of potassium phosphate dibasic, 0.2 g of magnesium sulfate (pentahydrate), 50 g of cholic acid, 5 g of sodium hydroxide, and 1 g of sodium carbonate were dissolved in 1 liter of purified water and the mixture was then sterilized at 121° C. for 15 minutes to prepare the culture medium (pH 8: cholic acid 5% (w/v)).

Twenty ml of the medium was dispensed to a test tube (3 φ×20 cm), to which was aseptically added 1 ml of the bacterial culture that had been grown by shaking at 37° C. for 20 minutes in a test tube containing 20 ml of the culture medium having the same composition as above except that cholic acid and sodium hydroxide had been excluded therefrom. This was then cultured by shaking at 37° C. for 4 days and then was centrifuged to remove the cellular mass. The supernatant thus obtained was acidified by adding thereto dilute sulfuric acid. The formed precipitate was harvested and dried to obtain 0.98 g of a white powder. An portion of the product was subjected to high performance liquid chromatography to determine the production ratio of ursocholic acid, cholic acid, and 7-ketodeoxycholic acid. The ratio was found to be ursocholic acid 71.8%, cholic acid 14.0%, and 7-ketodeoxycholic acid 14.2%.

EXAMPLE 2

The same procedure was followed as in Example 1 except that the amount of cholic acid was 1% (w/v) and that of sodium hydroxide was 0.1% (w/v) in the culture medium of Example 1 and the culturing time was 20 hours. The composition of the product obtained after cultivation was determined to be ursocholic acid 75.0%, cholic acid 8.4%, and 7-ketodeoxycholic acid 16.6%.

EXAMPLE 3

The same procedure was followed as in Example 1 except that the amount of the culture medium of Example 1 was 40 ml, the culturing time was 3 days, and the culturing method was incubation. The composition of the product obtained after cultivation was determined to be ursocholic acid 63.6%, cholic acid 35.0%, and 7-ketodeoxycholic acid 0.9%.

EXAMPLE 4

The same procedure was followed as in Example 3 except that the amount of cholic acid was 1% (w/v) and that of sodium hydroxide was 0.1% (w/v) in the culture medium of Example 3. The composition of the product obtained after cultivation was determined to be ursocholic acid 82.3%, cholic acid 17.4%, and 7-ketodeoxycholic acid 0.3%.

EXAMPLE 5

The same procedure was followed as in Example 4 except that cholic acid in the culture medium of Example 4 was replaced with 7,12-diketolithocholic acid. The composition of the product obtained after cultivation was determined to be ursocholic acid 75.2%, cholic acid 19.0%, 12-ketodeoxycholic acid 1.4%, and 7-ketodeoxycholic acid 4.2%.

EXAMPLE 6

The same procedure was followed as in Example 4 except that cholic acid in the culture medium of Example 4 was replaced with 7-ketodeoxycholic acid. The composition of the product obtained after cultivation was determined to be ursocholic acid 81.1%, cholic acid 16.5%, and 7-ketodeoxycholic acid 1.3%.

EXAMPLE 7

The same procedure was followed as in Example 4 except that cholic acid in the culture medium of Example 4 was replaced with $3\alpha,7\alpha$-dihydroxy-12-keto-$5\beta$-cholanic acid. The composition of the product obtained after cultivation was determined to be ursocholic acid 81.2%, cholic acid 15.7%, and 12-keto ursodeoxycholic acid 2.2%.

EXAMPLE 8

The same procedure was followed as in Example 4 except that cholic acid in the culture medium of Example 4 was replaced with chenodeoxycholic acid and the amount thereof was 0.2% (w/v). The composition of the product obtained after cultivation was determined to be ursodeoxycholic acid 63.1%, 7-ketolithocholic acid 3.2%, and chenodeoxycholic acid 33.5%.

EXAMPLE 9

The same procedure was followed as in Example 4 except that cholic acid in the culture medium of Example 4 was replaced with 7-ketolithocholic acid and the amount thereof was 0.5% (w/v). The composition of the product obtained after cultivation was determined to be ursodeoxycholic acid 73.5%, 7-ketolithocholic acid 8.5%, and chenodeoxycholic acid 16.0%.

INDUSTRIAL APPLICABILITY

As hereinabove described, there are provided a method for producing bile acids having a $7\beta$-hydroxyl group, said method comprising culturing Bacillus sp. TTUR 302 that belongs to the genus Bacillus and that have the ability of converting bile acids having a $7\alpha$-hydroxyl group or a 7-keto group into bile acids having a $7\beta$-hydroxyl group in a nutrient medium containing bile acids having a $7\alpha$-hydroxyl group or a 7-keto group to produce bile acids having a $7\beta$-hydroxyl group such as ursodeoxycholic acid in the culture, and then harvesting it.

The method of producing bile acids utilizing the invention organism is easy and safe to handle as compared to the conventional chemical methods of production. Furthermore, when compared to the method of production utilizing the conventional microorganisms, the invention organism is a facultative anaerobe that permits conversion to bile acids at the condition of a high substrate concentration even under the aerobic condition. The invention organism, therefore, is particularly useful in the commercial production. Furthermore, since the invention organism does not have the ability of causing hemolysis and producing lecithinase which may lead to pathogenicity of the organism, this is a safe method in terms of handling and culturing the microorganism and thus it is an excellent method.

What is claimed is:

1. A biologically pure culture of Bacillus Sp. TTUR 302, which is a facultative anaerobic microorganism, and is capable of converting bile acids having a $7\alpha$-hydroxyl group or a 7-keto group into bile acids having a $7\beta$-hydroxyl group, wherein the microorganism converts cholic acid into ursocholic acid at a conversion efficiency of at least 60% at a 5% substrate concentration and converts chenodeoxycholic acid into ursodeoxycholic acid at conversion efficiency of at least 60% at a 0.2% substrate concentration.

2. A method for producing bile acids having a $7\beta$-hydroxyl group comprising the steps of:

culturing a facultative anaerobe Bacillus sp. TTUR 302 in a nutrient medium containing a bile acid having a $7\alpha$-hydroxyl group or a 7-keto group in order to produce a bile acid having a $7\beta$-hydroxyl group into the medium; and harvesting said bile acid having a $7\beta$-hydroxyl group from the medium.

3. The method for producing bile acids having a $7\beta$-hydroxyl group according to claim 2, wherein said bile acids having a $7\beta$-hydroxyl group is $3\alpha,7\beta$-dihydroxy-$5\beta$-cholanic acid, $3\alpha,7\beta$-dihydroxy-12-ketocholanic acid, or $3\alpha,7\beta,12\alpha$-trihydroxy-$5\beta$-cholanic acid.

4. The method for producing bile acids having a $7\beta$-hydroxyl group according to claim 2, wherein the nutrient medium containing the bile acids have a pH in the range of 8 to 10.

5. The method according to claim 2, wherein, in said step of culturing, said nutrient medium contains cholic acid, and said bile acid having a $7\beta$-hydroxyl group comprises ursocholic acid.

6. The method according to claim 5, wherein said cholic acid is present in said nutrient medium at a concentration of 5%.

7. The method according to claim 2, wherein, in said step of culturing, said nutrient medium contains chenodeoxycholic acid, and said bile acid having a $7\beta$-hydroxyl group comprises ursodeoxycholic acid.

8. The method according to claim 5, wherein said chenodeoxycholic acid is present in said nutrient medium at a concentration of 0.2%.

9. A biologically pure culture of a facultative anaerobe Bacillus sp. TTUR 302.

* * * * *